(12) United States Patent
Wang

(10) Patent No.: US 8,520,207 B2
(45) Date of Patent: Aug. 27, 2013

(54) DETECTION SYSTEM FOR BIREFRINGENCE MEASUREMENT

(75) Inventor: Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 0 days.

(21) Appl. No.: 13/588,352

(22) Filed: Aug. 17, 2012

(65) Prior Publication Data

US 2012/0326005 A1 Dec. 27, 2012

Related U.S. Application Data

(63) Continuation of application No. 12/442,490, filed as application No. PCT/US2007/079501 on Sep. 26, 2007, now Pat. No. 8,248,605.

(60) Provisional application No. 60/827,026, filed on Sep. 26, 2006.

(51) Int. Cl.
| G01J 4/00 | (2006.01) |
| G01B 9/00 | (2006.01) |
| G01N 21/41 | (2006.01) |
| B60Q 1/14 | (2006.01) |
| G05D 25/02 | (2006.01) |
| H03G 3/20 | (2006.01) |

(52) U.S. Cl.
USPC .......... 356/365; 356/364; 356/124; 356/128; 250/214 D; 250/214 AG

(58) Field of Classification Search
None
See application file for complete search history.

(56) References Cited

U.S. PATENT DOCUMENTS

| 2,773,413 | A | * | 12/1956 | Schade, Sr. | 356/124 |
| 3,447,874 | A | * | 6/1969 | Back | 356/124.5 |
| 3,502,413 | A | * | 3/1970 | Lightner | 356/309 |
| 3,544,796 | A | * | 12/1970 | Baker | 250/201.1 |
| 3,714,372 | A | * | 1/1973 | Rosen et al. | 348/79 |
| 4,050,085 | A | * | 9/1977 | Prince et al. | 348/217.1 |
| 4,307,294 | A | * | 12/1981 | Campbell | 250/201.7 |
| 5,028,125 | A | * | 7/1991 | Kikuchi | 359/452 |
| 5,239,171 | A | * | 8/1993 | Takabayashi et al. | 250/205 |
| 6,266,141 | B1 | * | 7/2001 | Morita | 356/365 |
| 6,985,288 | B2 | * | 1/2006 | Miyashita et al. | 359/385 |
| 7,609,958 | B2 | * | 10/2009 | Border et al. | 396/89 |

FOREIGN PATENT DOCUMENTS

JP 11095126 A * 4/1999

* cited by examiner

*Primary Examiner* — Gordon Stock, Jr.
(74) *Attorney, Agent, or Firm* — Hancock Hughey LLP

(57) ABSTRACT

A system for controlling a light beam in an optical setup includes a light source that directs a collimated light beam along a path, through a sample, and toward the active area of a stationary detector. A lens is selectively movable into the path of the light beam for spreading the beam in instances where the path of the beam is altered by the sample between the source and the stationary detector. The detector, therefore, is held stationary. Adjustment mechanisms are provided for increasing the intensity characteristic of the light that reaches the detector to account for a decrease in intensity that occurs when the lens is in the path of the light beam to spread the beam.

8 Claims, 2 Drawing Sheets

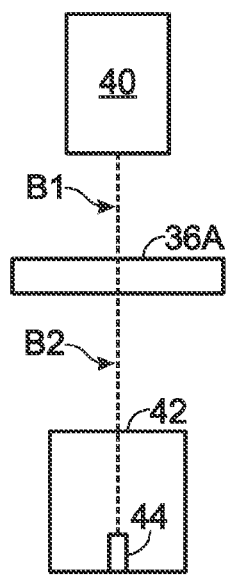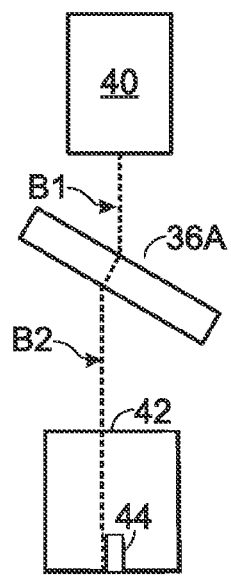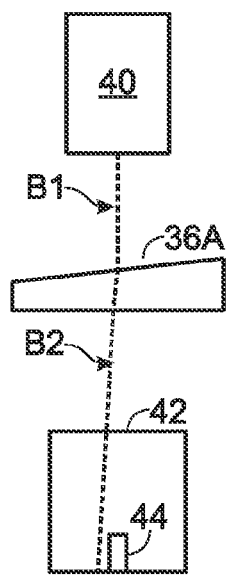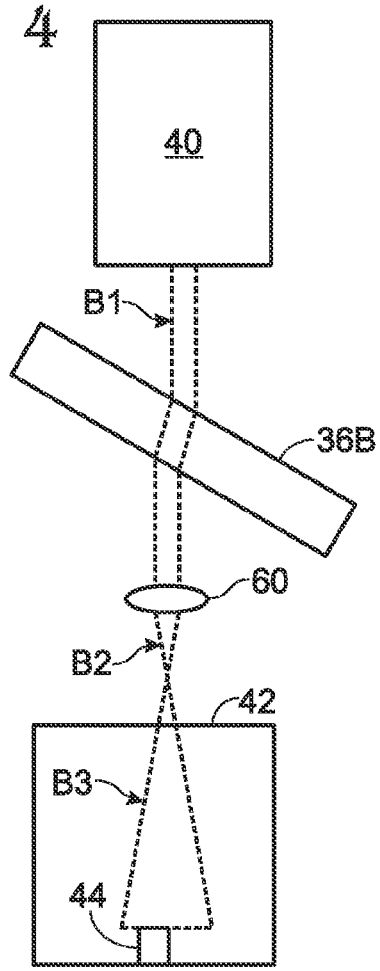

DETECTION SYSTEM FOR BIREFRINGENCE MEASUREMENT

FIELD OF THE INVENTION

This invention relates to birefringence measurement systems.

BACKGROUND OF THE INVENTION

An exemplary birefringence measurement system is described in U.S. Pat. No. 6,985,227. A schematic diagram of the optical setup 20 of one embodiment of such a system is shown in FIG. 1. That system employs as a light source 22 a polarized He—Ne laser having a wavelength of 632.8 nm. The light beam B1 from the source 22 passes through a polarizer 24 oriented at 45 degrees. The system also includes a photoelastic modulator ("PEM") 26 oriented at 0 degrees and operated at 50 KHz.

A sample holder 34, which can be mounted on a computer-controlled X-Y stage is provided, thereby to allow the beam to scan various locations of an optical element or sample 36.

The light beam 82 that emanates from the sample (for convenience hereafter referred to as the "sampled beam" B2) is directed through another PEM 28 that is oriented at 45 degrees and operated at 60 KHz. After passing through an analyzer 30 oriented at 0 degrees, the sampled beam B2 is directed into the receiving or active area of a Si-photodiode detector 32.

The light source beam (in this case, laser light) is well collimated, and compact detectors (that is, having relatively small active areas on the order of 1-6 mm) may be employed, especially where the sample 36 has parallel surfaces normal to the incident light beam B1. Also, birefringence characteristics of thin samples, such as thin films, may also be effectively measured with such a system, even though the sample may be tilted relative to the source beam, such that the incident angle of the beam is oblique to the surface of the sample.

There are certain applications, however, where the sample thickness or shape will have the effect of refracting the beam B1 in a manner such that the sampled beam B2 emanating from the sample will not align with the active area of the detector. In this regard, reference is made to FIGS. 2A-2C.

FIGS. 2A-2C show as a module 40 the combined light source 22, polarizer 24 and PEM 26 mentioned above. Similarly, the second PEM 28, analyzer 30 and detector 32 are shown as a single module 42. FIG. 2A shows a collimated light beam B1 emanating from a generally parallel-surfaced sample 36A that is oriented with its surfaces normal to the incident light beam B1. The sample will not significantly alter the direction of the incident beam, and the sampled beam B2 will thus be incident upon the active area 44 of the detector, which is essentially aligned with the light source beam B1.

FIG. 2B illustrates an application where, for example, a relatively thick sample 36B is held so that it is tilted as respects the incident beam B1, which has the effect of redirecting the sampled beam B1 so that beam does not impinge upon the active area 44 of the detector. A similar misalignment is shown in FIG. 2C where a wedge-shaped sample 36C has the effect of realigning the sampled beam B2 by an amount such that the active area 44 of the detector fails to detect the intensity or other characteristics of the beam B2. The signal processing components of the birefringence measurement system noted above require this information for analyzing the birefringence characteristics of the sample.

The present invention provides a simple, versatile, and low-cost technique for ensuring that the information carried in the sampled beam B2 is directed to the active area of the detector, thereby enabling effective birefringence measurement of a variety of sample shapes and sizes.

BRIEF DESCRIPTION OF THE DRAWINGS

FIGS. 2A-2C are block diagrams of birefringence measurement systems and illustrating variations in sampled beam paths B2 resulting from variations in the sample size or orientation.

FIG. 4 is a diagram illustrating another embodiment of the detection system of the present invention

DETAILED DESCRIPTION

Figure 3:
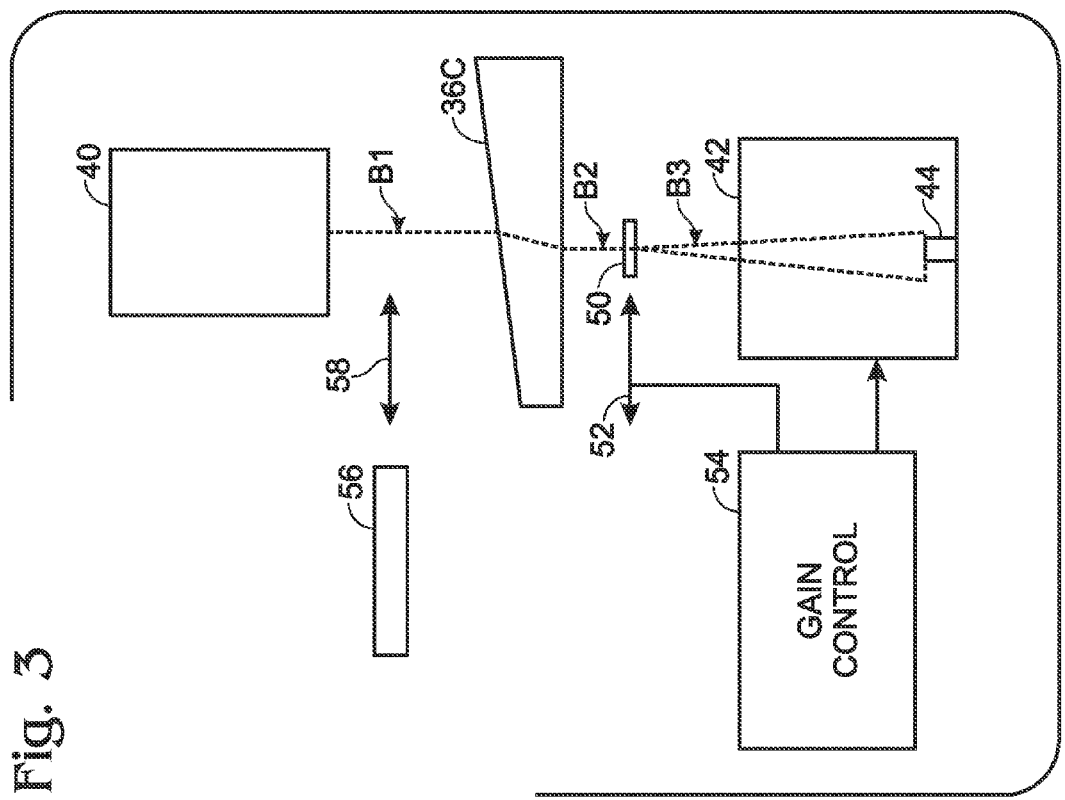
FIG. 3 is a diagram illustrating one embodiment of the detection system of the present vention.
Figure 1:
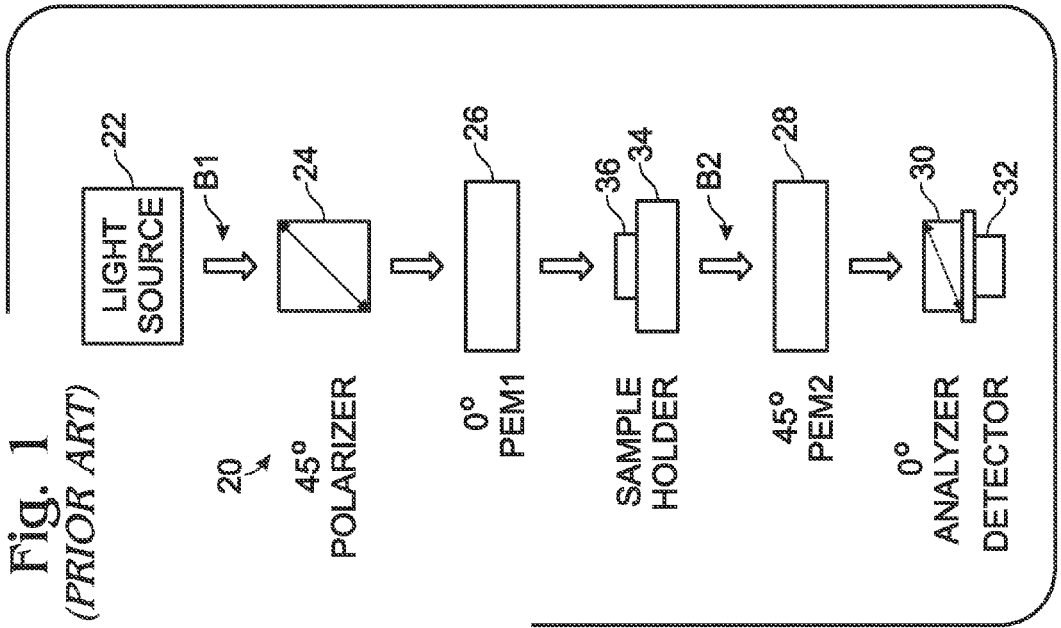
FIG. 1 is a block diagram of a birefringence measurement system with which the present detection system may be employed.

FIG. 3 depicts the primary components of the detection system as incorporated into the setup generally depicted in FIG. 2C, where a wedge-shaped sample 36C has the effect of realigning the sampled beam B2 by an amount that, in the absence of the present invention, would cause that beam to substantially miss (fail to impinge upon) the active area 44 of the detector.

The embodiment of FIG. 3 includes a lens 50 located in the path of the sampled beam B2 so that the otherwise collimated, narrow sampled beam B2 is spread, diverged or defocused in a manner such that a sufficient amount of the beam B3 will indeed impinge upon the detector active area 44 for providing the beam intensity and other information required by the overall birefringence measurement system.

Preferably, the lens 50 is mounted for selective movement into or out of the path of the sampled beam B2, as indicated by the arrow 52. Such movement can be accomplished by any suitable translating or rotating holder for the lens 50. It will be appreciated that the use of such selective lens motion will enable the same detector to be used with samples that do not substantially alter the beam path (FIG. 2A) by moving the lens to a position that is retracted from the beam path, and with samples that do alter the beam path (FIGS. 2B and 2C, for example) by extending the lens into the path of the beam, as seen in FIG. 3. As the sample position changes (hence changing the beam path) the lens position will also be changed as needed to ensure it remains in the path of the beam.

It is noteworthy here that the intensity level of the portion of the diverged light beam B3 impinging upon the active area 44 of the detector will be relatively less than that of the sampled beam in applications where the beam remains narrow and collimated (FIG. 2A). As one aspect of this invention, therefore, the detector gain is adjusted to account for changes in beam intensity that arise when the lens is moved into or out of the beam path as noted above. This ensures that the output of the detector is optimized, irrespective of whether the diverging lens is used.

Preferably, the detector gain is automatically controlled 54 and correlated to the motion of the lens. For example, in instances where the lens control mechanism extends the lens into the beam path, a corresponding control or feedback signal to the gain control 54 would adjust the detector gain accordingly.

An alternative to the detector gain adjustment just discussed is also illustrated in FIG. 3. In this alternative the intensity of the source beam B1 would be adjusted depending upon whether the lens 50 is in place to diverge the beam as described above. In this approach the detector gain is fixed, and the source beam intensity is modified by the presence or absence of a neutral density filter 56 in its path. For example, when the lens 50 is extended to create the diverged beam B3 discussed above, the filter 56 (the extension and retraction movement 58 of which may be automatically controlled and inversely correlated to that of the lens 50) will be in a retracted mode as shown in FIG. 3 so that the beam intensity reaching the detector will be greater as compared to when the neutral density filter is in the path of beam B1. In this regard, the filter 56 is extended into the beam path when the lens 50 is retracted therefrom. It will be appreciated that the use of the retractable neutral density filter as just described ensures that the beam impinging upon the detector does so with substantially the same intensity irrespective of whether the beam diverging lens 50 is present in the path.

A diverging or negative lens 50 is illustrated in FIG. 3. FIG. 4 illustrates the use of a positive lens 60 (with the size of the beam B1 enlarged for clarity) for imparting the beam divergence discussed above. It will be appreciated that the selection and location of the lenses 50, 60 may be theoretically or empirically established for any of a number of sample configurations.

It is contemplated that the present invention is useful in any system using a collimated light source, and is not limited to laser-based systems.

The invention claimed is:

1. A light detector system, comprising:
   a source producing a collimated light beam that travels along a path;
   a detector including a gain control and having an active area aligned with the beam path for receiving the light beam and providing as output an indication of an intensity characteristic of the received beam;
   a defocusing lens mounted for movement into and out of the path of the light beam and controllable for moving the lens into the path of the beam, the lens being configured to defocus the beam that is received by the detector; and
   wherein the system includes gain adjustment means associated with the lens and operable in response to the lens position for adjusting the gain of the detector.

2. The system of claim 1 wherein the lens is configured to be a negative lens.

3. The system of claim 1 wherein the lens is configured to be a positive lens.

4. The system of claim 1 wherein the detector is mounted to be stationary relative to the light source.

5. The system of claim 1, further comprising a translating or rotating holder to which the lens is mounted for movement.

6. A light detector system, comprising:
   a source producing a collimated light beam that travels along a path;
   a detector having an active area aligned with the beam path for receiving the light beam and providing as output an indication of an intensity characteristic of the received beam;
   a defocusing lens mounted for movement into and out of the path of the light beam and controllable for moving the lens into the path of the beam, the lens being configured to defocus the beam that is received by the detector; and
   adjustment means for adjusting the intensity characteristic of the light beam depending upon whether the lens is in the path of the light beam.

7. The system of claim 6 wherein the adjustment means comprises a neutral density filter movable into and out of the path of the light beam whenever the lens is respectively moved out of and into the path of the light beam.

8. The system of claim 6, further comprising a translating or rotating holder to which the lens is mounted for movement.

\* \* \* \* \*